United States Patent [19]

Yoon

[11] Patent Number: 4,990,152
[45] Date of Patent: Feb. 5, 1991

[54] APPLICATOR DEVICE HOUSING MULTIPLE ELASTIC LIGATURES IN SERIES AND FOR DILATING AND APPLYING ELASTIC LIGATURES ONTO ANATOMICAL TISSUE

[76] Inventor: InBae Yoon, 2101 Highland Ridge Dr., Phoenix, Md. 21131

[21] Appl. No.: 256,639

[22] Filed: Oct. 12, 1988

[51] Int. Cl.⁵ .................................................. A61B 17/12
[52] U.S. Cl. .................................................... 606/140
[58] Field of Search ................... 128/326, 303 A, 831, 128/843; 606/141, 140, 139

[56] References Cited

U.S. PATENT DOCUMENTS

| 1,400,653 | 12/1921 | Barbour | 606/139 |
| 3,155,094 | 11/1964 | Hamilton | 606/140 |
| 3,687,138 | 8/1972 | Jarvik | 606/139 |
| 3,870,048 | 3/1975 | Yoon . | |
| 3,911,923 | 10/1975 | Yoon . | |
| 3,967,625 | 7/1976 | Yoon | 128/303 A X |
| 3,989,049 | 11/1976 | Yoon . | |
| 4,085,743 | 4/1978 | Yoon . | |
| 4,103,680 | 8/1978 | Yoon . | |
| 4,257,420 | 3/1981 | Terayama | 128/303 A |
| 4,267,839 | 5/1981 | Laufe et al. | 128/303 A |
| 4,374,523 | 2/1983 | Yoon . | |
| 4,471,766 | 9/1984 | Terayama . | |
| 4,493,319 | 1/1985 | Polk et al. | 128/303 A |
| 4,598,711 | 7/1986 | Deniega | 128/326 |

Primary Examiner—Michael H. Thaler

[57] ABSTRACT

An elastic ligature applicator device including a central member for storing a plurality of unexpanded elastic ligatures in series fashion, a conical expander and a ligature dilator for pushing a ligature over the expander and onto grasped anatomical tissue. An optional applicator manipulation facilitating assembly may be provided to ease use of the applicator device during a surgical procedure. Components are readily disassembled to load a series of unexpanded elastic ligatures onto the applicator device.

14 Claims, 2 Drawing Sheets

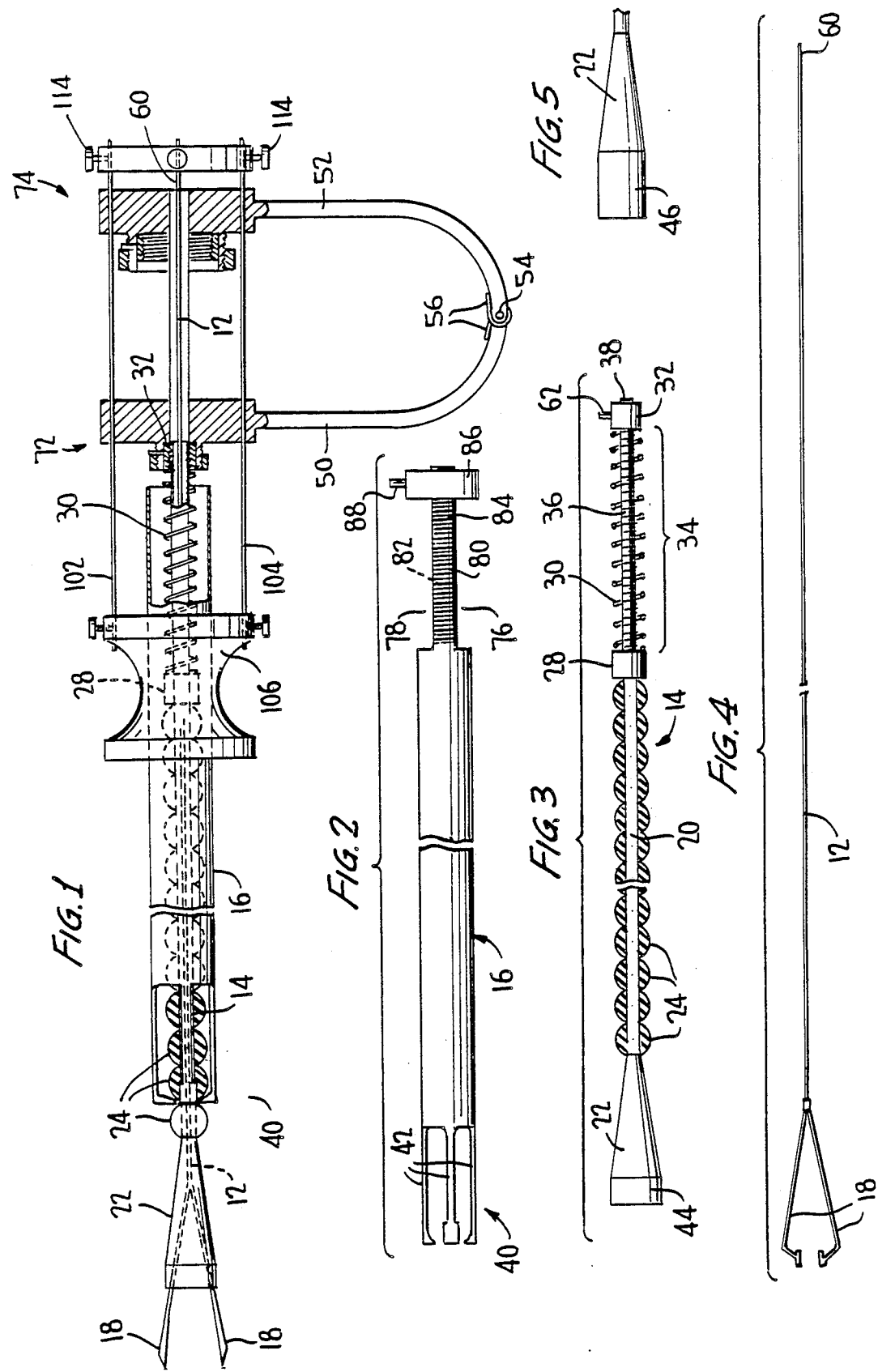

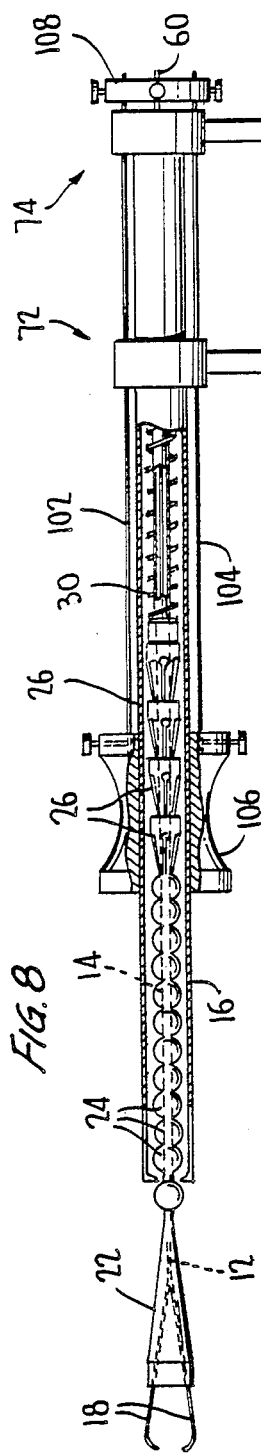
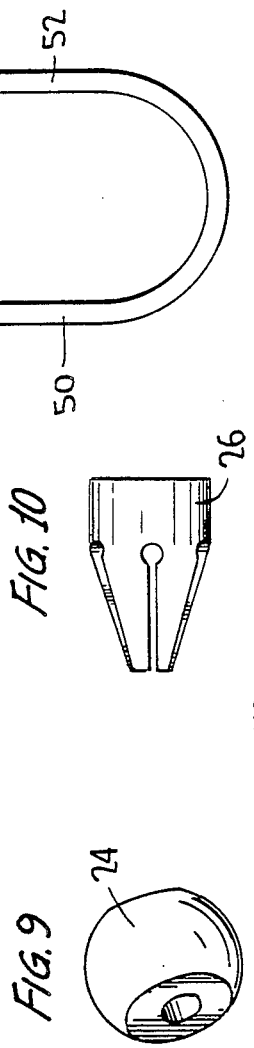
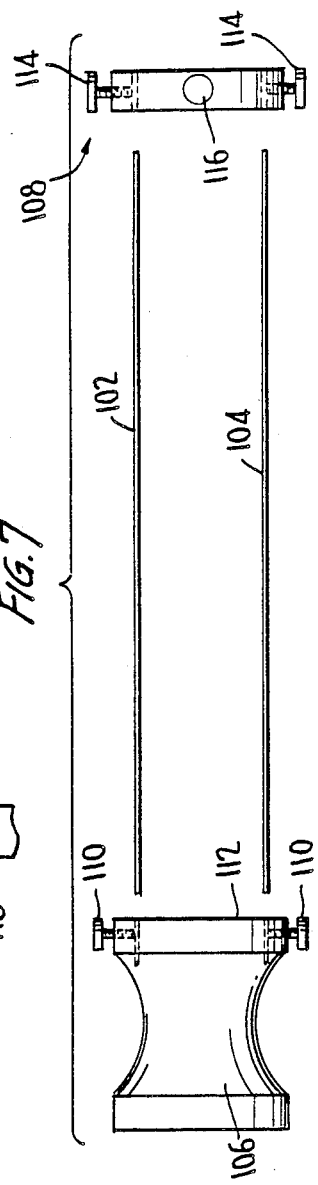
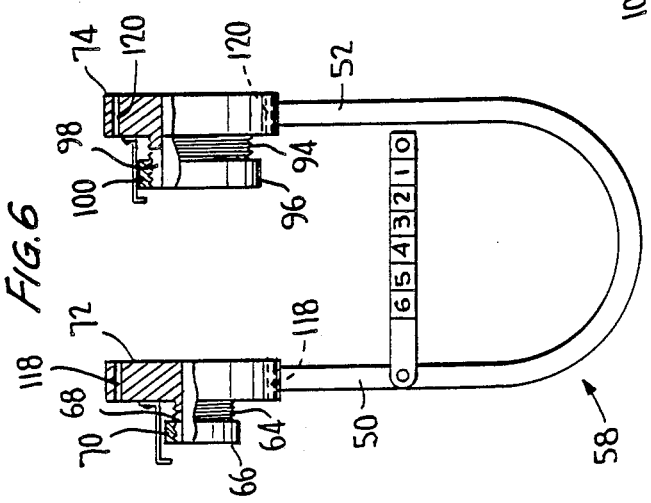

APPLICATOR DEVICE HOUSING MULTIPLE ELASTIC LIGATURES IN SERIES AND FOR DILATING AND APPLYING ELASTIC LIGATURES ONTO ANATOMICAL TISSUE

BACKGROUND OF THE INVENTION

This invention relates generally to surgical devices and, more particularly, to an improved elastic ligature applicator having a central member for storing a plurality of elastic ligatures in series and in an unexpanded state, an elastic ligature conical expander and a ligature dilator for pushing a ligature over the expander and onto grasped anatomical tissue. An optional handle assembly facilitates manipulation of the applicator during a surgical procedure. Components are readily assembled and disassembled to load a new supply of ligatures into the applicator.

Several prior art patents and pending applications are directed to somewhat similar applicators. U.S. Pat. No. 4,167,188 issued to Coy L. Lay, deceased, et al only discloses an elastic band designed and dimensioned for tying off human Fallopian tissue or similar anatomical tubular tissue. My own prior U.S. Pat. No. 4,548,201 is directed to an improved, elastic ligating ring clip and a ring loader for placing elastic rings onto the distal end of a ring applicator. The loader includes a conical ring expander and a ring dilator in the form of thin, flexible parts joined in pairs radiating from a deformable, elastic ring engaging aperture.

Relating pending applications include my copending U.S. applications Ser. Nos. 049,503, filed May 14, 1987, now U.S. Pat. No. 4,788,966, and 063,913, filed June 19, 1987 now U.S. Pat. No. 4,860,746. The former application concerns multi-functional instruments for surgical procedures including improved stretchable ligating and occluding devices, an applicator and an expanding and loading device somewhat similar to that disclosed in my prior U.S. Pat. No. 4,548,201. The latter application is directed to improved elastic ring clips, with which the present invention may be used, and an improved loading device for expanding and loading an elastic ring onto an applicator, in an expanded state.

Elastic rings or ligatures with which the present invention may be used may be made from a wide variety of known absorbable and non-absorbable materials which are discussed in detail below. A problem that has been noted is that at least some of these materials have an abbreviated elastic memory life. In other words, if rings or ligatures made of elastic material are stretched or expanded and left on the applicator for too long a period of time, then the elastic memory of the material may be impaired so that, when an elastic ligature is placed onto anatomical tissue, it may not return to its initial shape or configuration. Thus, the intended ligating or occluding function of the ligature may be impaired.

The present invention, in direct contradistinction to prior devices, provides an elastic ligature applicator for storing a series of ligatures in a substantially unexpanded state. The ligature is stretched or expanded only immediately prior to placement of the ligature onto anatomical tissue. Thus, the possibility of impairment of the elastic memory characteristic of the material from which the ligature is made is reduced to a virtual nullity.

SUMMARY OF THE INVENTION

Accordingly, it is a principal object of the invention to provide an applicator device for storing one or more unexpanded elastic ligatures and for expanding or stretching a ligature only immediately prior to application of the ligature onto anatomical tissue.

It is another object of the invention to provide an applicator device for elastic ligatures including a central member for spring loading a series of one or more unexpanded elastic ligatures, a conical, open-ended expander, an inner member and forceps instrument for grasping and drawing anatomical tissue onto the open end of the conical expander, and an elastic ligature dilator for pushing a ligature over the conical expander and onto the grasped anatomical tissue.

It is a further object of the invention to provide an applicator device for elastic ligatures which is readily assembled and disassembled to load another series of ligatures into the applicator device.

It is yet another object of the invention to provide an applicator device for elastic ligatures and an optional handle assembly to facilitate manipulation of the applicator device during a surgical procedure.

BRIEF DESCRIPTION OF THE DRAWINGS

Further and more complete objects and advantages of the invention will become readily apparent by reference to the following detailed specification and drawings in which:

FIG. 1 is a side, elevational partly sectional view of a preferred embodiment of the ligature applicator device of this invention;

FIG. 2 is a side, elevational view of the outer tubular member of the applicator device, which has an elastic ligature dilator on its distal end;

FIG. 3 is a side elevational view of the central, tubular member of the applicator device, having a central body for storing unexpanded elastic ligatures and a conical ligature expander at its distal end;

FIG. 4 is a side elevational view of an inner member of the applicator device and having a forceps at its distal end.

FIG. 5 is a detail, side elevational view of another embodiment of the elastic ligature conical expander;

FIG. 6 is a side elevational view of the U-shaped handle component of the applicator device;

FIG. 7 is a side elevational, exploded view of the component of the optional handle assembly, for facilitating manipulation of the applicator device during a surgical procedure;

FIG. 8 is a side elevational partly sectional view of another embodiment of the ligature applicator device of this invention;

FIG. 9 is a perspective view of a spherically configured elastic ligature which may be applied with the instant invention;

FIG. 10 is a side, elevational view of another elastic ligature which may be applied with this invention, the ligature being a ring clip; and FIG. 11 is an enlarged side elevational view of the upper mounting end of the distal handle member.

DESCRIPTION OF THE PREFERRED EMBODIMENTS

Referring now to the drawings by reference character and, in particular to FIGS. 1-4 thereof, an embodiment of the applicator device 10 is shown, including an inner elongate member 12 (FIG. 4) telescopically received within a middle tubular member 14 which, in turn, is received within an outer tubular member 16. In the sense of the drawing figures, the applicator and components thereof each have a distal end at the left and a proximal end at the right.

As best shown in FIG. 4, inner member 12 has a forceps 18 at its distal end made of material having sufficient elastic memory so as to be spring urged into a normally open configuration as shown. The term "forceps" is intended to include any type of gripping or holding means including suction means or the like. Forceps 18 could further include, if desired, biopsy box members (not shown).

Referring now to FIG. 3, central tubular member 14 is made up of a central elongate body portion 20 and a conical elastic ligature expander 22 on the distal end of body portion 20. Body portion 20 and conical expander 22 may be of integral, one-piece construction. Body portion 20 has an external diameter of predetermined dimension so that a plurality of centrally apertured unexpanded elastic ligatures may be received thereon, in end-to-end series fashion as shown. The elastic ligature may be made from a wide variety of absorbable or non-absorbable materials and may have any one of a wide variety of configurations. For purposes of illustration in the instant application, the elastic ligature may be a centrally apertured, spherically configured ligature 24 (as best shown in FIG. 9) or it could be an expandable ring clip 26 (as best shown in FIG. 10). Further details of ligature 24 are set forth in my above-referenced copending application Ser. No. 063,913 and several embodiments of suitable, expandable ring clips are disclosed in my above-referenced copending application Ser. No. 049,503; both said applications are incorporated herein by reference.

Referring further to FIG. 3, a plurality of elastic ligatures, for example, spherical elastic ligatures 24, are received or loaded onto central body portion 20. An abutment member 28 is loaded onto body portion 20 behind the last of the ligatures 24. Member 28 is centrally apertured so that member 28 is slidable along body portion 20. A coil compression spring 30 is located proximally of abutment member 28 and an adjustable stop member 32 is located at the proximal end of body portion 20. The proximal portion 34 of body portion 20 is externally threaded as indicated at 36 and stop member 32 includes a matingly internally threaded lumen 38. Thus, stop member 32 is threaded onto body portion 20 distally a sufficient distance to exert a distal spring load onto the series of ligatures 24. Also, member 32 may be removed so that a series of ligatures may be loaded onto central body portion 20. More specifically, member 32 is threaded off of proximal portion 34 and spring 30 and abutment member 28 are removed. A series of ligatures are loaded onto body portion 20. Abutment member 28 followed by spring 30 are reloaded onto body portion 20 and member is threaded onto portion 34 a sufficient distance to exert a spring load onto the series of ligatures 24, for reasons detailed below.

Referring now to FIG. 2, outer tubular member 16 includes an elastic ring dilator at its distal end, made by longitudinally splitting the member 16 distal end 40 into a plurality of fingers 42. Movement of outer tubular member 16 and fingers 42 distally with respect to middle tubular member 14 causes fingers 42 to engage the proximal side of a ligature 24 located forwardly or distally thereof (FIG. 1) and push the ligature along, over and beyond the conical ring expander 22; of course, as the ligature is forced along expander 22, it will be stretched open.

During a surgical procedure, with parts assembled as shown in FIG. 1, inner member 12 is manipulated so that forceps 18 are positioned to grasp anatomical tissue (e.g., vascular tissue) in the operative field. Movement of inner member 12 proximally with respect to middle tubular member 14 and conical expander 22 causes grasped tissue to be drawn in looped fashion within an open, cylindrical base 44 of conical expander 22; thereafter, a ligature 24 is moved over and beyond the distal end of base 44 by the dilator fingers 42 so that the ligature 24 "snaps" back to its original configuration, thus effectively ligating the looped tissue. Depending on the dimensions of the tissue to be ligated, the length dimension of base 44 may be relatively long, as shown at 46 in FIG. 5. The length dimension of the base 44 or 46 is predetermined to suit conditions in the operative field as just explained.

Turning now to FIGS. 1 and 6, a graspable U-shaped handle assembly 48 is provided for moving outer tubular member 16 over middle tubular member 14 to effect expansion and ejection of a ligature over looped anatomical tissue as explained above. U-shaped handle assembly 48 includes a pair of handle members 50 and 52. Handle assembly 48 may be bifurcated centrally at 54, as shown in FIG. 1, and provided with a leaf spring 56 to urge the handle members 50 and 52 apart. Alternatively, the U-shaped handle assembly may be of one-piece, spring material construction as indicated at 58 in FIG. 6.

The handle assembly 48 may be operatively associated with gauge means for controlling and visually indicating the ejection of each ligature from the middle member 14. Such gauge means is disclosed in my copending application Ser. No. 049,503, the disclosure of which is incorporated herein by reference.

The assembly of parts discussed so far may now be explained. Middle member 14 is loaded with a plurality of ligatures as set forth above. Inner member 12 is inserted in middle member 14 so that the proximal end 60 of member 12 extends through the stop member 32 (as shown in FIG. 1). With reference to FIG. 3, stop member 32 includes an upwardly directed post 62. Stop member 32 is mounted onto handle member 50 as follows As seen in FIG. 6, the upper end of handle member 50 includes a distally directed, externally threaded socket 64 and matingly internally threaded capture nut 66. Socket 64 has a slot 68 therein, and nut 66 has a slot 70 therein. With slots 68 and 70 aligned as shown, stop member 32 is inserted into socket 64 so that post 62 is located rearwardly or proximally of nut 66. The nut is then threaded proximally to capture and secure end member 32 tightly, against upper mounting end 72 of handle member 50.

Referring now to FIGS. 2 and 6, the proximal end of outer tubular member 16 will be attached to the upper end of handle member 52, against its upper mounting end 74. As shown in FIG. 2, the proximal portion of outer tubular member 16 is slotted at 76 and 78, thus to form two wings 80 and 82. The proximal end 84 of member 16 is threaded as illustrated and nut 86 with a post 88 is threaded onto end 84 as shown. The nut 86 is removed and tubular member 16 is slid over the assembled members 12 and 14. Wings 80, 82 are passed over nut 66 and socket 64 (FIG. 6) and through mating slots 90, 92 shown in FIG. 11 formed through mount 72. Nut 86 is then threaded onto end 84 of member 16 with post 88 disposed vertically. Mount 74 includes a distally directed externally threaded socket 94 and a matingly, internally threaded capture nut 96. Socket 94 is slotted at 98 and nut 96 is slotted at 100. With slots 98 and 100 aligned as shown, nut 86 is inserted into socket 94 so that post 88 is located rearwardly or proximally of nut 96. The nut is then threaded proximally to capture and secure nut 86 and post 88 tightly, against upper mounting end 74 of handle member 52.

Turning again to FIG. 1, it can be seen that a squeezing action on handle members 52, 50 causes outer tubular member 16 to move distally with respect to middle member 14, thus to move, expand and expel a ligature from the applicator on to looped tissue, all as explained above When handle members 50 and 52 are released, member 16 moves proximally over member 14 and fingers 42 spread slightly over the next ligature 24 in the series and then come to rest behind the ligature 24, as shown in FIG. 1. The next ligature is in place against the apex of conical expander 22 because of the loading force exerted by coil compression spring 30.

Referring now to FIGS. 1 and 7, an optional handle assembly for facilitating manipulation of the applicator 10 will be discussed. This handle assembly is especially useful for manipulating forceps 18 to grasp tissue as explained earlier. The assembly includes a pair of control rods 102, 104, arranged generally parallel to a proximal portion of outer tubular member 16 as shown in FIG. 1, a spool-shaped graspable handle 106, mounted for sliding movement along a mesial portion of member 16, and a proximally disposed control rod locking member 108. Spool handle 106 includes thumb screws 110 for readily attaching and detaching the distal ends of control rods 102, 104 in the proximal face 112 of handle 106 and locking member 108 has similar thumb screws 114 for readily attaching and detaching the proximal ends of control rods 102, 104 therein. Locking member 108 also includes a central locking lumen 116 for attaching the proximal end 60 of inner member 12 thereto.

One method of assembly of the optional handle assembly is as follows. Spool handle 106 is slipped onto outer tubular member 16 and control rods 102, 104 are attached by thumb screws 110. Control rods 102, 104 are then slipped through upper and lower bores 118 formed through mount 72 on handle member 50 and upper and lower bores 120 formed through mount 74 on handle member 52. Locking member 108 is then attached to the proximal ends of control rods 102, 104 by thumb screws 114 and the proximal end 60 of inner member 12 is locked into lumen 116. Obviously, other steps of assembly could be used to mount the handle, control rods and locking member onto the applicator.

Returning to FIG. 1, it can be seen that, in use, handle 48 can be grasped by one hand and spool handle 106 may be grasped by the other hand. Movement of handle 106 distally causes forceps 18 to be extended as shown. After tissue is grasped, proximal movement of handle 106 causes the forceps 18 to move proximally and draw tissue within the conical expander.

The handle assembly just explained is said to be optional because the inner member 12 and forceps 18 could be manipulated during a surgical procedure by grasping the handle 48 with one hand and proximal end 60 of inner member 12 with the fingers of the other hand.

Turning now to FIG. 8, another embodiment 122 of the invention is shown which has the same features of construction and operation as the embodiment of the invention illustrated in FIG. 1. However, the overall appearance of this embodiment is somewhat streamlined with respect to the embodiment of FIG. 1. Also, FIG. 8 illustrates the loading of two varieties of elastic ligatures into the applicator 122, these being, for example, spherical ligatures 24 and ring clips 26. The point is that the invention may be loaded with clips similar to each other or different from one another.

With further reference to the material from which the ligatures 24, 26 are made, it could be selected from any one of the following special medical grade families. These families include dimethylpolysaloxane, polyurethane, stainless steel, latex rubber, Teflon (polytetrafluoroethylene), or any other medical grade, stretchable material family so long as the material has substantially 100% elastic memory. In the event, the material selected does not have the required elastic memory, the material could be coated or impregnated with a suitable medical grade material in order to render the ligature useful.

The ligatures are implantable permanently or non-permanently on tissue organ structures, animal or human. They may be used as ligatures in such procedures as tubal ligation, vas ligation, blood vessel ligation and any organ structure strangulation procedure. Since the ligatures are, generally, ring-shaped, they can be used to ligate any anatomical tubular structure by being placed about a looped tubular structure. This is accomplished by manipulating forceps 18 to engage a tubular structure and then withdraw the structure within the base of the conical expander 22 to create a loop in the tubular structure. Thereafter, a ligature 24 or 26 is slipped over the looped tubular structure.

In summary, the ligatures are useful in the following procedures: female tubal ligation, male vasectomy, bleeding vessel ligature, polypectomy, hemorrhoidectomy, uterine suspension (by shortening round ligaments), and any surgical blood vessel ligature procedures, human or animal.

This invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

I claim:

1. An applicator device for housing and applying one or more apertured elastic ligatures to anatomical tissue, the applicator device comprising: an inner elongate member telescopically received within a middle tubular member which, in turn, is telescopically received within an outer, elongate tubular member, said inner, middle and outer members each having a distal end and a proximal end, said inner member having forceps means mounted on said distal end thereof, said middle tubular member including central, elongate body portion means for receiving one or more elastic ligatures thereon in end to end series fashion, said central body portion means having a distal end, a proximal end and an external diameter for receiving one or more elastic ligatures thereon in a relaxed, substantially unexpanded state, a ligature abutment member slidably mounted on said central body portion means for engaging the proximal one of the one or more elastic ligatures loaded onto said central body portion means, compression spring means on and adjacent said central body portion means proximal end and located proximally of said abutment member for distally spring loading elastic ligatures onto said middle member central body portion means, an externally threaded portion on said proximal end of said middle member and a spring stop member defining a matingly internally threaded aperture therethrough threaded on said threaded portion of said middle member proximally of said compression spring means, whereby the loading force created by said compression spring means may be varied by threading said stop member along said threaded portion of said middle member proximal end, a conically shaped elastic ligature expander at said distal end of said middle member central body portion means and having an apex and an open base, said conical expander apex adjoining said central body portion distal end, said distal end of said outer tubular member including means defining elastic ligature dilator means for engaging an apertured ligature and pushing it over said conical ligature expander, whereby anatomical tissue is ligated by manipulating said inner member so that said forceps means engages tissue, moving said inner member proximally with respect to said middle member thus to draw anatomical tissue into said conical expander base, manipulating said outer member dilator means to engage an apertured ligature, and moving said outer member distally with respect to said middle member to push an engaged ligature over said conical expander and beyond said conical expander open base to engage anatomical tissue.

2. The applicator device as claimed in claim 1 wherein said middle tubular member central body portion means and said conical expander are of integral, one-piece construction.

3. The applicator device as claimed in claim 1 wherein said conical expander open base comprises an open cylinder having a predetermined length dimension into which anatomical tissue may be drawn by said forceps means.

4. The applicator device as claimed in claim 1 wherein said means defining elastic ligature dilator means includes longitudinal splits formed in said outer tubular member distal end, thus defining a plurality of elastic ligature engaging fingers.

5. The applicator device as claimed in claim 1 further comprising U-shaped handle means having, a first handle member attached to said middle tubular member and a second handle member attached to said outer tubular member whereupon a grasping, squeezing action on said U-shaped handle means causes said outer tubular member to move distally with respect to said middle tubular member thus to cause said ligature dilator means to push a ligature along and over said conical expander.

6. The applicator device as claimed in claim 5 wherein said first handle member is readily detachably connected to said middle tubular member proximal end and said second handle member is readily detachably connected to said outer tubular member proximal end.

7. The applicator device as claimed in claim 5 wherein said handle means further includes gauge means for controlling and visually indicating the ejection of each ligature from the applicator device.

8. The applicator device as claimed in claim 5 wherein said U-shaped handle means is of integral, one-piece, resilient material construction.

9. The applicator device as claim in claim 5 and further comprising applicator device manipulation facilitating means including a pair of control rods disposed along and generally parallel to a proximal portion of said outer tubular member, said control rods each having a distal end and a proximal end, said control rod proximal ends extending proximally beyond said outer tubular member proximal end, a graspable handle surrounding and slidable along a mesial portion of said outer tubular member and having a proximal face on one side thereof, said control rod distal ends being attached to said graspable handle proximal face, a control rod locking member attached to said control rod proximal ends, and means for slidably mounting the upper ends of the U-shaped handle means handle members on said control rods.

10. The applicator device as claimed in claim 9 wherein said control rod locking member further includes means defining a central locking lumen therethrough, said inner member proximal end extending into and engaged within said central locking lumen whereby, during a surgical procedure, said graspable handle may be moved distally with respect to said outer tubular member thus to move said forceps distally beyond said conical expander open base and, after manipulation of the applicator device to grasp anatomical tissue with said forceps, said graspable handle may be moved proximally with respect to said outer tubular member, thus to draw grasped anatomical tissue into said conical expander open base.

11. The applicator device as claimed in claim 9 further comprising first readily detachable locking means for mounting said control rod distal ends onto said graspable handle proximal face and second readily detachable locking means for mounting said control rod proximal ends onto said control rod locking member.

12. In combination, at least one apertured elastic ligature and a device for applying said at least one apertured elastic ligature to anatomical tissue comprising elongate applicator means having a proximal end and a distal end including means disposed between said proximal and distal ends of said applicator means for storing said at least one elastic ligature in a relaxed, substantially unexpanded state, means for positioning anatomical tissue in a ligating position adjacent said distal end of said applicator means, means for expanding said at least one elastic ligature and positioning said elastic ligature about the anatomical tissue in the ligating position, and means disposed at said proximal end of said applicator means for operating said expanding and positioning means whereby said at least one elastic ligature is stored in a relaxed, substantially unexpanded state prior to engagement with anatomical tissue for ligation thereof.

13. A device as claimed in claim 12 wherein said expanding and positioning means includes a conically shaped ligature expander having an apex for receiving a ligature from said storing means and dilator means operable by said operating means for pushing a ligature along said expander.

14. A device as claimed in claim 13 and further comprising a plurality of said apertured elastic ligatures stored in relaxed, substantially unexpanded states in said storage means.